(12) United States Patent
Brown et al.

(10) Patent No.: US 6,859,215 B1
(45) Date of Patent: Feb. 22, 2005

(54) METHOD, SYSTEM AND PROGRAM FOR SPECIFYING AN ELECTRONIC FOOD MENU ON A DATA PROCESSING SYSTEM

(75) Inventors: Michael Wayne Brown, Georgetown, TX (US); Kelvin Roderick Lawrence, Round Rock, TX (US); Michael A. Paolini, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/466,000

(22) Filed: Dec. 17, 1999

(51) Int. Cl.[7] .............................................. G09G 5/00
(52) U.S. Cl. ......................... 345/811; 705/15; 705/26
(58) Field of Search ................................. 345/811, 745, 345/760, 810, 744, 968; 705/15, 26

(56) References Cited

U.S. PATENT DOCUMENTS

| | | | |
|---|---|---|---|
| 5,412,564 A | | 5/1995 | Ecer |
| 5,559,313 A | | 9/1996 | Claus et al. |
| 5,664,110 A | * | 9/1997 | Green et al. .................... 705/1 |
| 5,727,153 A | * | 3/1998 | Powell ........................ 235/375 |
| 5,845,263 A | * | 12/1998 | Camaisa et al. .............. 705/27 |
| 5,899,502 A | * | 5/1999 | Del Giorno ................. 283/117 |
| 5,969,316 A | * | 10/1999 | Greer et al. ................. 235/375 |
| 5,991,739 A | * | 11/1999 | Cupps et al. ................. 705/26 |
| 6,026,377 A | * | 2/2000 | Burke ........................ 235/383 |
| 6,047,327 A | * | 4/2000 | Tso et al. .................... 709/202 |
| 6,068,183 A | | 5/2000 | Freeman et al. |
| 6,087,927 A | * | 7/2000 | Battistini et al. ...... 340/286.06 |
| 6,088,681 A | * | 7/2000 | Coleman et al. ............... 705/1 |
| 6,123,259 A | * | 9/2000 | Ogasawara .................. 235/380 |
| 6,129,274 A | * | 10/2000 | Suzuki ....................... 235/380 |
| 6,208,976 B1 | * | 3/2001 | Kinebuchi et al. ............ 705/15 |
| 6,236,974 B1 | * | 5/2001 | Kolawa et al. ................ 705/7 |
| 6,246,998 B1 | * | 6/2001 | Matsumori .................. 345/810 |
| 6,301,564 B1 | * | 10/2001 | Halverson .................... 705/15 |
| 6,334,109 B1 | * | 12/2001 | Kanevsky et al. ............ 705/14 |
| 6,366,220 B1 | * | 4/2002 | Elliott ....................... 340/10.1 |
| 6,401,034 B1 | * | 6/2002 | Kaplan et al. .............. 340/988 |
| 6,405,034 B1 | * | 6/2002 | Tijerino ...................... 455/412 |
| 6,434,530 B1 | * | 8/2002 | Sloane et al. ............... 235/383 |

OTHER PUBLICATIONS

QuikOrder Press Release, "San Diegans First to Use Domino's Pizza New On–Line Ordering Through QuikOrder.com", Nov. 1999. (Internet Screen Dumps).*

* cited by examiner

*Primary Examiner*—Sy D. Luu
(74) *Attorney, Agent, or Firm*—Marilyn Smith Dawkins; Dillon & Yudell LLP

(57) ABSTRACT

Multiple food menu items are retrieved from a data storage medium by a data processing system with access to the data storage medium via a communications medium. The multiple food menu items are compared with previously stored food preferences for a particular customer. A food menu is selected, wherein the food menu items that satisfy said food preferences for said particular customer are distinguished, such that an electronic food menu is specified for a particular customer.

76 Claims, 10 Drawing Sheets

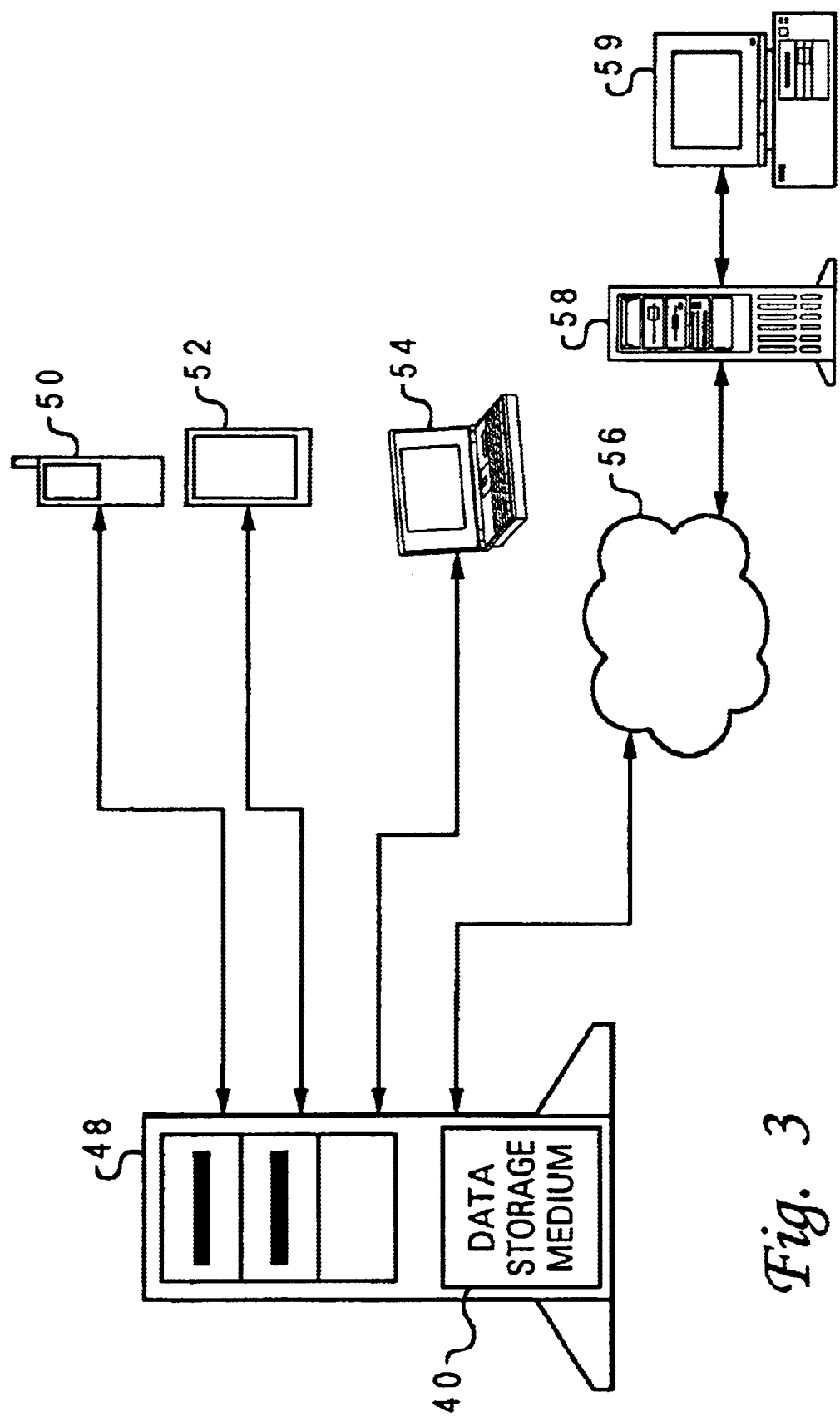

| # | Name | Price | Type of Currency | Desc | Heart Smart | Overall Dietary Daily Values | Ingredients | Amounts and Addl ingred. | Alcohol | Caffeine | Organic/Free Range | Kosher | Vegan | Dietary Daily Values |
|---|---|---|---|---|---|---|---|---|---|---|---|---|---|---|
| 1 | Dish 1 | 2.00 | US Dollar | Cup of hot, steamy soup | Yes | Serving Size | Water | 4 oz. | No | No | - | - | - | |
|  |  |  |  |  |  | Calories | Chicken | 1/2 lb. | No | No | Yes | No | No | |
|  |  |  |  |  |  | %Fat | Green chiles | 1 cup | No | No | Yes | - | Yes | |
|  |  |  |  |  |  | %Carbohydrates | Salt | 2 tsp | No | No | - | - | - | |
|  |  |  |  |  |  | %Sodium Vitamins |  |  |  |  |  |  |  | |
| 1 | Dessert 1 | 5.00 | US Dollar | Hot apples with brandy | No | Serving Size | Apples | 1 cup | No | No | Yes | - | Yes | |
|  |  |  |  |  |  | Calories | Cinnamon | 2 tbs | No | No | - | - | - | |
|  |  |  |  |  |  | %Fat | Sugar | 1/2 cup | No | No | - | - | No | |
|  |  |  |  |  |  | %Carbohydrates | Brandy | 1/4 cup | Yes | No | - | - | No | |
|  |  |  |  |  |  | %Sodium Vitamins |  |  |  |  |  |  |  | |
| 2 | App 1 | 7.00 | US Dollar | Cheesy dip | No | Serving Size | American cheese | 2 cups | No | No | Yes | - | No | |
|  |  |  |  |  |  | Calories | Tomatoes | 1 cup | No | No | Yes | - | Yes | |
|  |  |  |  |  |  | %Fat | Onions | 1/2 cup | No | No | Yes | - | Yes | |
|  |  |  |  |  |  | %Carbohydrates | Cilantro | 1/4 cup | No | No | Yes | - | Yes | |
|  |  |  |  |  |  | %Sodium Vitamins |  |  |  |  |  |  |  | |

Fig. 4

| | Key ID | Age | Price Range | Ingred. to avoid | Currency Pref. | Special Inst. | Alcohol | Caffeine | Heart Smart | Organic | Kosher | Protein | Fat | Calories | Security Pref. |
|---|---|---|---|---|---|---|---|---|---|---|---|---|---|---|---|
| 74 | 1 | 24 | 2.00-6.00 | Apples | US Dollars | No burning | - | - | Yes | Yes | - | Less than 10g | Less than 20g | Less than 300 calories | None |
| 76 | 905 | 80 | 2.00-20.00 | Lima beans | US Dollars | None | No | No | Yes | - | Yes | More than 10g | Less than 15g | More than 400 calories | Block ID |

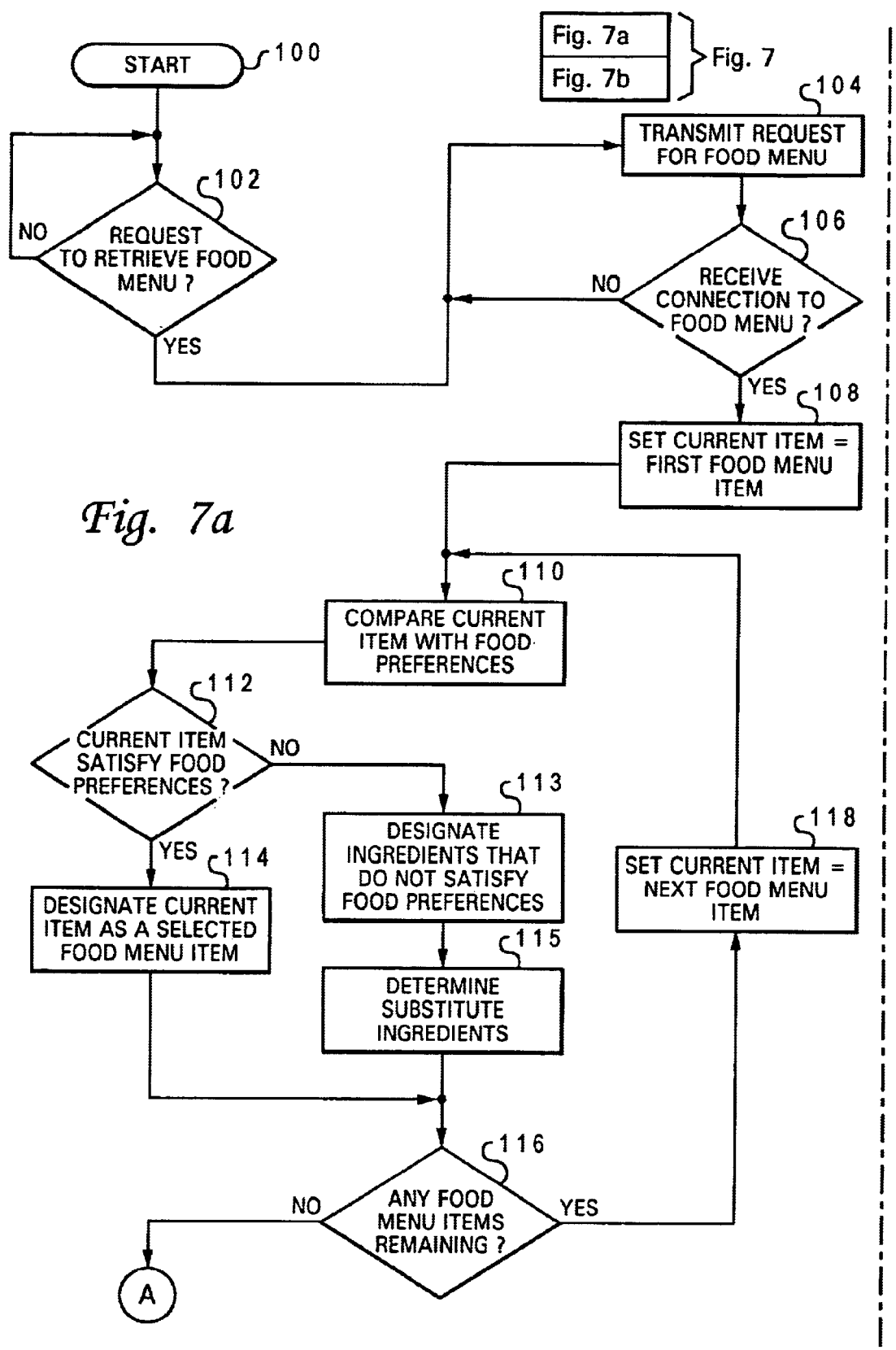

METHOD, SYSTEM AND PROGRAM FOR SPECIFYING AN ELECTRONIC FOOD MENU ON A DATA PROCESSING SYSTEM

CROSS-RELATED PATENT APPLICATION

The present invention is related to the subject matter of the following commonly assigned, copending United States patent applications identified as application numbers: 09/465,999 and 09/466,051. The content of the above-referenced applications is incorporated herein by reference.

BACKGROUND OF THE INVENTION

1. Technical Field

The present invention relates in general to an improved method, system and program for presenting a food menu electronically, and in particular to a method, system and program for efficiently specifying an electronic food menu. Still more particularly, the present invention relates to a method, system and program for specifying an electronic menu for a particular customer on a data processing system.

2. Description of the Related Art

The global economy has made the business of selling more competitive than ever. Businesses that do not maximize customer satisfaction and profitability will typically not survive in today's markets. Businesses are therefore demanding tools and methods to provide their competitive edge.

In the area of food sales, maximizing customer satisfaction is particularly important to businesses. It is commonly recognized that what and when a person eats has a great impact on a person's overall health and well being. Therefore, in maximizing customer satisfaction, there has been a shift towards providing the customer with menus that provide for customer needs. For example, many menus indicate entrees for heart health conscious customers.

In addition to heart healthy selections, other factors come together for customers selecting from a menu. For example a customer may make menu selections based on personal health reasons such as diabetes, heart disease, food allergies and sensitivity to heart burn. In addition, a recovering alcoholic or one who avoids caffeine may select items that do not include these substances. In another example, a customer may select food based on philosophical reasons, such as selecting foods that are only grown organically. Alternatively, an entree's assumed aesthetic effect on the body may effect a customer's selection depending on whether the customer is attempting to lose or gain weight. Further, religious reasons may frequently prohibit not only what can be eaten and when, but how the food is prepared.

While there have been efforts to provide more information about food on a menu, it is typically difficult to know what one is eating, when dining out or purchasing preprocessed food. Some menus now include a list of some ingredients and some waiters may know the main ingredients of dish, however finding out a list of every ingredient and preparation thereof is typically not available or there is not an efficient way for the information to be provided. Likewise, requesting actions that deviate from the norm are often miscommunicated enroute to the cooking/preparation staff. For example, requesting that an ingredient, like onions, be removed.

Another difficulty in purchasing food for some can be the way that a menu is provided. For example, seeing-impaired customers typically have difficulty reading a menu in restaurants and other food venues. In addition, when in a foreign country, menus in a language understood by the customer may not be available. Moreover, when in a foreign country converting currency to determine the relative expense of an item in one's typical currency can be time consuming.

Therefore, in view of the aforementioned, it would be preferable to provide a method for customers to easily attain a list of menu items which meet their ordering criteria and menu items which do not meet their ordering criteria. In addition, it would be preferable to provide a method for cooking/preparation staff to receive customer's orders with any special requests in an efficient manner. Further, it would be preferable to provide a method for rendering a menu such it is easily understandable according to a user's preferences.

SUMMARY OF THE INVENTION

In view of the foregoing, it is therefore an object of the present invention to provide an improved method, system and program for presenting a food menu electronically.

It is another object of the present invention to provide a method, system and program for efficiently specifying an electronic food menu.

It is yet another object of the present invention to provide a method, system and program for specifying an electronic food menu for a particular customer on a personal data processing system.

In accordance with the method, system and program of the present invention, multiple food menu items are retrieved from a data storage medium by a data processing system with access to the data storage medium via a communications medium. The multiple food menu items are compared with previously stored food preferences for a particular customer. A food menu is selected, wherein the food menu items that satisfy said food preferences for said particular customer are distinguished, such that an electronic food menu is specified for a particular customer.

All objects, features, and advantages of the present invention will become apparent in the following detailed written description.

DESCRIPTION OF THE DRAWINGS

The invention itself, as well as a preferred mode of use, further objects, and advantages thereof, will best be understood by reference to the following detailed description of an illustrative embodiment when read in conjunction with the accompanying drawings, wherein:

FIG. 3 depicts multiple types of computer systems which may be utilized to specify an electronic food menu in accordance with the method an system of the present invention;

FIG. 4 illustrates a block diagram of a storage structure for food menu items in accordance with the method and system of the present invention;

FIG. 5 depicts a block diagram of a storage structure for a selection of food preferences in accordance with the method and system of the present invention;

DESCRIPTION OF THE PREFERRED EMBODIMENT

The present invention may be executed in a variety of systems, including a variety of computers under a number of different operating systems. The computer may be, for example, a personal computer, a personal digital assistant, a network computer, a midrange computer or a mainframe computer. In addition, the computer may be a stand-alone system or part of a network such as a local-area network (LAN) or a wide-area network (WAN). Therefore, in general, the present invention is preferably executed in a computing device that performs computing tasks such as manipulating data in storage that is accessible to the computing device. In addition, the computing device preferably includes at least one output device and at least one input device.

Figure 1:
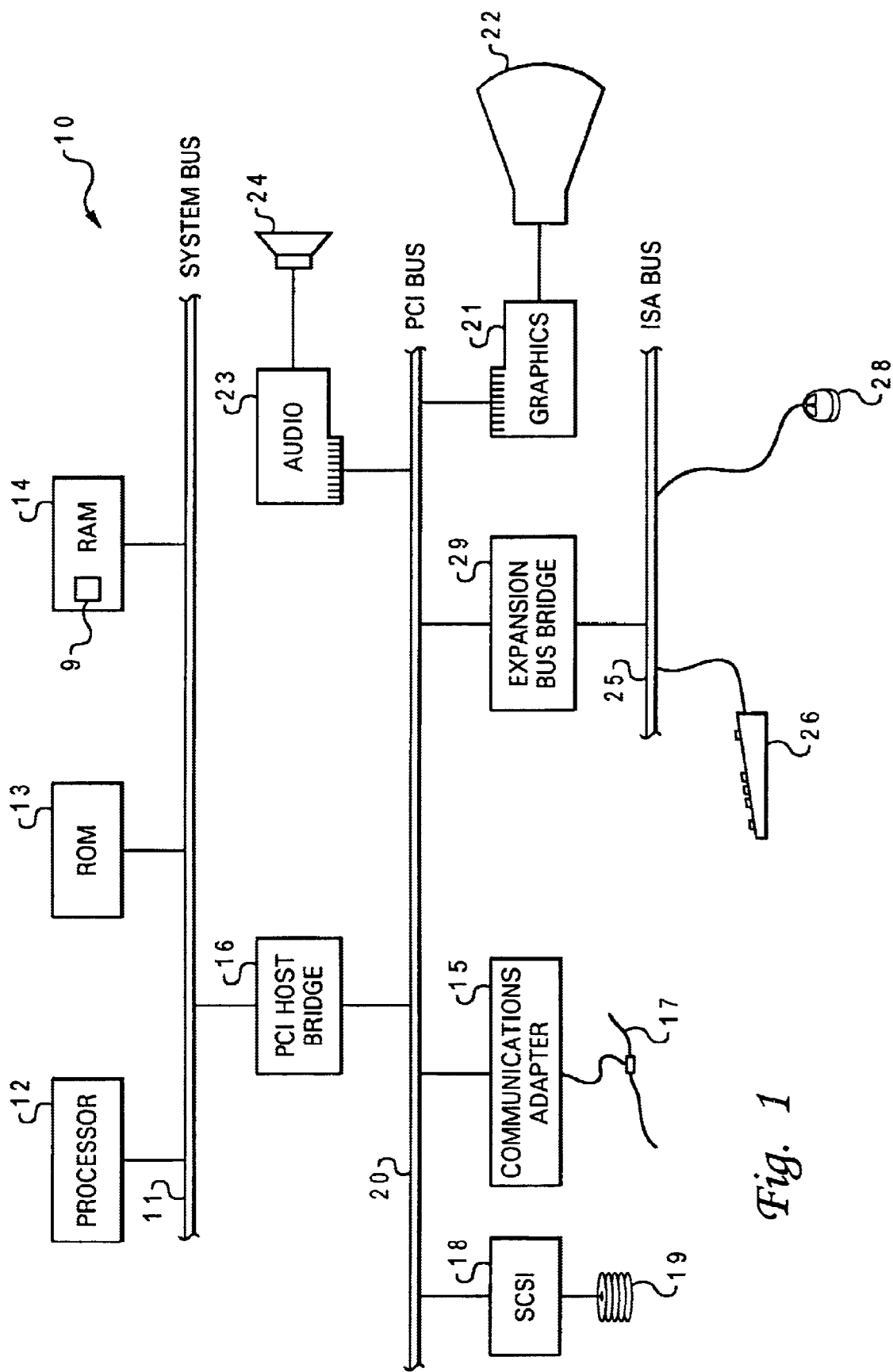
FIG. 1 depicts a block diagram of a typical computer system that may utilize a preferred embodiment of the present invention.

Referring now to the drawings and in particular to FIG. 1, there is depicted a block diagram of a typical computer system that may utilize a preferred embodiment of the present invention. As shown, a processor (CPU) 12, a read-only memory (ROM) 13, and a Random-Access Memory (RAM) 14 are connected to a system bus 11 of a computer system 10. CPU 12, ROM 13, and RAM 14 are also coupled to a PCI local bus 20 of computer system 10 through a PCI host bridge 16. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

Also attaching to PCI local bus 20 are communications adapter 15, small computer system interface (SCSI) 18, and expansion bus bridge 29. In the present embodiment, communications adapter 15 is for connecting computer system 10 to a network 17. In alternate embodiments, communications adapter 15 may provide for communicating via wireless transmissions, including but not limited to, radio frequency (RF) transmissions or infrared transmissions.

SCSI 18 is utilized to control high-speed SCSI disk drive 19. Alternatively, other types of data storage medium may be utilized. Expansion bus bridge 29, such as a PCI-to-ISA bus bridge, may be utilized for coupling ISA bus 25 to PCI local bus 20. As shown, a keyboard 26 and a mouse 28 are attached to ISA bus 25 for performing certain basic I/O functions. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

Computer system 10 also preferably includes an interface such as a graphical user interface (GUI) and an operating system (OS) that reside within machine readable media to direct the operation of computer system 10. Any suitable machine-readable media may retain the GUI and OS, such as RAM 14, ROM 13, SCSI disk drive 19, and other disk and/or tape drive (e.g. magnetic diskette, magnetic tape, CD-ROM, optical disk, or other suitable storage media). Any suitable GUI and OS may direct CPU 12. For example, the AIX operating system is one of IBM's operating systems which may be implemented.

Further, computer system 10 preferably includes at least one software application (e.g. program product) that resides within machine readable media, for example menu specification application 9 in RAM 14. A software application contains instructions that when executed on CPU 12 carry out the operations depicted in the flowcharts of FIG. 7, FIG. 8, and others described herein.

Figure 2:
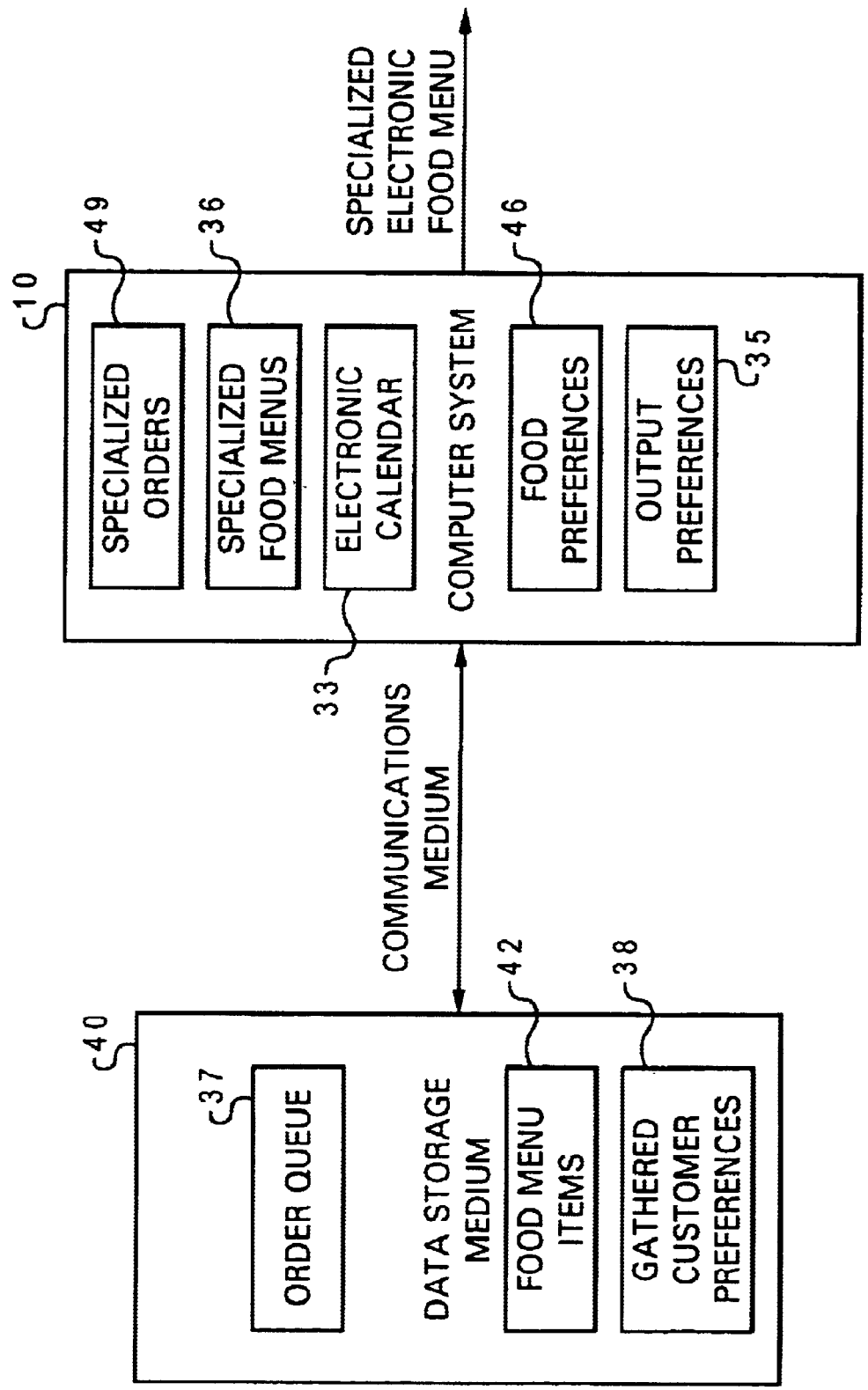
FIG. 2 illustrates a system for selecting an electronic food menu in accordance with the method and system of a preferred embodiment of the present invention.

With reference now to FIG. 2, there is depicted a system for selecting an electronic food menu in accordance with the method and system of a preferred embodiment of the present invention. As depicted, a data storage medium 40 comprises a database of food menu items 42. Preferably the database of food menu items 42 comprises multiple food menu names with descriptions, prices, ingredients, ingredient quantities, preparation techniques and other food/health data for each food menu item.

In accordance with the present invention, a computer system 10 communicates with data storage medium 40 via a communications medium. In addition, computer system 10 communicates with other data processing systems (not shown) via a communications medium. The communications medium may comprise wireless communications, network communications, a wired connection or other communication media that enables transmission of data to and from computer system 10 and data storage medium 40. In addition, computer system 10 is preferably enabled to communicate via multiple communications media. Wireless RF communications are preferably supported by the Bluetooth or other RF transmission specification.

Data exchange across the communications medium is preferably supported by a data transmission protocol such as extensible mark-up language (XML). In addition, a data translation file such as a document type definition (DTD) or schema is preferably provided to validate and translate the XML data. Moreover, a style sheet such as an XSL file is preferably utilized to provide a display specification for the XML data. In addition, a web page or other network graphical interface may be accessed in order to access the XML data. For example, a particular restaurant may provide a web page for accessing the XML encoded data that includes food menu items 42 and other data.

Computer system 10 preferably includes stored food preferences 46 that are specified for a single user or multiple users. Food preferences 46 may include a specified price range for meals, ingredients to avoid, preparation preferences, current medications and selections of other food and health criteria such as a preference for heart smart meals. Food preferences 46 may include food preferences for a single customer or multiple customers. In alternate embodiments, food preferences 46 may be stored in a data storage medium that is externally or remotely accessible by computer system 10. In addition, computer system 10 may communicate through a communications medium with other computer systems to download food preferences to and from those computer systems. Food preferences 46 and other transmittable data stored on computer system 10 is preferably efficiently stored in a particular data transmission protocols such as XML.

Multiple levels of security may be specified for each set of food preferences 46 stored on computer system 10. For example, a shield from personal data stored with food preferences 46 such as a name, phone number, address, etc. may be shielded from transmittal and access. As will be understood by one well known in the art, multiple types of security methods and filters may be applied to food preferences 46 and other data on computer system 10.

According to the method and system of the preferred embodiment, computer system 10 retrieves food menu items 42 from data storage medium 40, compares food menu items 42 with food preferences 46, and selects a food menu wherein those food menu items which satisfy food preferences 46 are designated. Computer system 10 then outputs the specified electronic food menu. Alternatively, a food menu of food menu items 42 may be output by computer system 10 without designating particular food menu items. For example, when no food preferences are designated, a food menu of all food menu items without food preference based designation may be provided.

In some cases, food menu items that do not satisfy food preferences 46 may be able to satisfy food preferences 46 if a particular ingredient or ingredients are removed or if a replacement ingredient is utilized. For example, at a restaurant that serves chocolate milkshakes, a customer that specifies no caffeine in their food preferences would receive a specified electronic food menu where caffeine would be shown as the reason the food menu item does not satisfy their food preferences. In addition, the electronic food menu would show specifically that the chocolate syrup in the food menu item contains the caffeine. The customer may then order the chocolate milkshake with an indication not to add chocolate syrup. In the same example, the chocolate milkshake may be made with 2% milk that has a greater amount of fat per serving than the food preferences for the customer allow. The specified electronic food menu would indicate that the milkshake does not satisfy the food preferences because of the fat content of the milk. The customer may then request that skim milk be utilized in making the milkshake instead of 2% milk.

Preferably, as a customer removes or substitutes ingredients, the overall dietary value of a food menu item is recalculated and other fields are updated in order that the food menu item can be compared with the food preferences again and the specified electronic food menu updated. In addition, as the customer selects food menu items, an overall dietary value of the food menu items selected is preferably calculated.

The specified electronic food menu may be output to multiple peripherals. Examples of peripherals may include, but are not limited to a graphical display, an audio speaker, a tactile-detectable device, or a printer. In addition, computer system 10 may include output preferences 47 that are specified for a single user or multiple users. Output preferences 47 may include, but are not limited to specifications such as the size of font in a graphical display, the type of tactile-detectable output (e.g. Braille), the language, or the currency. The specified electronic food menu is preferably output in accordance with any output preferences 47.

In addition, the values displayed for the specified electronic food menu may be rendered in multiple formats according to output preferences 47. For example, only those food menu items that are designated may be displayed. Alternatively, all food menu items are displayed, but those food menu items that are not selected are indicated graphically. In addition, under those items that do not satisfy food preferences 46, ingredients that do not satisfy food preferences 46 may be graphically distinguished. Alternatively, food menu items are displayed in a sequential format where the best selection is displayed first and the worst selected displayed last. In addition, alternative coloring and highlights may be utilized to distinguish food menu items. For example, all food menu items that are designated are highlighted in bright green and those food menu items that are not designated are highlighted in bright red. Moreover, additional information about ingredients and other food and health related data may be available if selected by the customer.

The specified electronic food menu may include designations of daily specials, such as the Monday special. In addition to graphically distinguishing specials, daily specials may be automatically added to an electronic calendar 33 enabled on computer system 10. In the example of the Monday special, electronic calendar 33 can provide a reminder of the Monday special each Monday. Moreover, along with food menu items 42, coupon items and special offers may be transmitted with food menu items 42. For example, a coupon that is available for use during that restaurant visit or another may be transmitted with food menu items 42. If not utilized during that visit, the coupon can be stored and utilized for a subsequent visit. Coupons may be filtered based on food preferences 46, such as an age-related coupon. Alternatively, calendar based coupons may be transmitted with the food menu items. For example, a coupon that can be utilized on a particular Thursday when four or more dine may be transmitted with the food menu items and added to electronic calendar 33 on computer system 10.

After displaying the specified electronic food menu, computer system 10 may receive input designating an order from the particular customer from the specified electronic food menu. In addition, the customer may designate a credit card number or other electronic money payment method. Computer system 10 transmits the electronic money payment data to data storage medium 40 or another payment controller. Data storage medium 40 requests validation of the electronic money payment, as is well known in the art. If approved, computer system 10 attaches any food preparation preferences that are designated in food preferences 46 and transmits the food order to an order queue 37 wherefrom a kitchen staff can access the order. The order queue may adjust waiting for orders by individual food preferences, group food preferences and other criteria. For example, the order queue may adjust waiting for orders based on the frequency that a customer orders from the restaurant. While in the present embodiment order queue 37 is included in data storage medium 40, in alternate embodiments, order queue 37 may be externally or remotely accessible by data storage medium 40 or stored in an alternate data storage medium.

Data storage medium 40 is preferably enabled to retrieve and store customer food preferences in a customer preference database 38. By gathering food preferences of customers ordering from a menu, a restaurant may utilize the data to adjust their menu to meet customer needs and preferences. Moreover, in knowing customer preferences, coupons and food menu items that are transmitted to the customer may be customized. For example, if a particular customer always orders two drinks, two sandwiches and two cookies, a special coupon may be transmitted to computer system 10 for that particular customer that gives a discount for ordering two drinks, two sandwiches and two cookies. In another example, the number of coffees a particular customer has purchased at a coffee shop may be recorded such that on the $10^{th}$ cup the customer receives a free coffee.

In addition, computer system 10 is preferably enabled to store specified electronic food menus 45 and specialized food orders 49 such that the menus can be recalled and reused at a later time and orders can be queued off-line. For example, if a family of four is planning which restaurant to eat at, computer system 10 can compare electronic food menus 45 with the food preferences for each member of the family. Each member of the family may transmit their food preferences from their computer system to one computer system 10 by infrared or other short-range transmission medium. The restaurant or restaurants that include food menu items that are suitable for all members of the family are designated by computer system 10. In addition, any stored coupons for those restaurants may be indicated. Moreover, each member of the family may determine an order from the specified electronic food menu and queue the orders on computer system 10. At the restaurant, the queued orders are automatically transmitted to order queue 37 for the kitchen.

In addition, a restaurant menu may be accessed on-line by computer system 10. A specified electronic food menu may be determined based on food preferences 46. In addition, an order of food menu items from the specified electronic food menu may be selected. The food order is queued on computer system 10 at customer order 49 such that the order can be automatically placed at the restaurant. This function is particularly useful for a parent restricting the eating of their child. The parent may select food menu items that the child may order at various restaurants or the school cafeteria from on-line access to the restaurant menus. These specified orders are queued for ordering when computer system 10 is presented at one of those restaurants. This function is also particularly useful for creating a diet plan where food preference regulated meals from selected restaurants can be queued on computer system 10 such that the customer automatically orders a meal on their diet plan at the selected restaurants. In an alternate example, a group of co-workers may each specify an order from a particular restaurant's menu accessed on-line and queue the orders with their electronic payment data on computer system 10. Upon arriving at the restaurant, the queued orders can be automatically retrieved from computer system 10 and transmitted to order queue 37. In addition, concurrent with transmitting the order, electronic payment data is transmitted.

Referring now to FIG. 3, there are illustrated multiple types of computer systems which may be utilized to specify an electronic food menu in accordance with the method an system of the present invention. In the present embodiment, data storage medium 40 is included as an internal storage medium that is accessible by a server 48. In alternate embodiments, data storage medium 40 may be external or remote to server 48 or an alternate data processing system.

Multiple types of computer systems can retrieve data from and transmit data to data storage medium 40 via a communications link with server 48. Examples of computer systems include, but are not limited to, pervasive devices such as a mobile telephone 50, a personal digital assistant (PDA) 52, and a portable computer system 54. In addition a computer system may include and a desktop computer 59 or other workstation. Although not depicted, each of these computer systems may include additional peripheral devices and may communicate with other computer systems.

As depicted, mobile telephone 50, PDA 52 and a portable computing system 54 are preferably enabled to communicate with server 48 via wireless transmissions. For example, mobile telephone 50 may utilize a wireless network communications link with server 48 via the Internet or other network. In another example, a personal digital assistant 52 may utilize an infrared or RF communications link with server 48. Alternatively, a desktop computer 59 may communicate with a server 58 via a network connection, whereby server 58 communications with server 48 via a network 56, such as the Internet. In yet another embodiment, a computer system, such as portable computing system 54 may utilize a wired transmission link directly to server 48. As previously described, the communications medium may be specified by multiple types of transmission specifications, such as Bluetooth. In addition, as previously described, data transmission across the communications medium may be supported by multiple data transmission protocols, such as XML.

With reference now to FIG. 4, there is illustrated a block diagram of a storage structure for food menu items in accordance with the present invention. As depicted, the food menu items corresponding to a menus from restaurants "1" and "2" are preferably stored in a data storage structure such as database 60. The example database 60 is provided in order to depict a selection of fields 62 which may be included in a data storage structure that is filterable. For the purposes of example, food menu items have been entered for rows 64, 66 and 68. In alternate embodiments, alternate selections of fields for defining food and health data for food menu items may be utilized. In addition, alternate types of data storage structures and methods may be utilized. Further, while not depicted, a graphical interface for entering a selection of fields 62 and food menu items is preferably provided.

As depicted in FIG. 4, fields 62 include multiple fields. For example, a menu number field designates to which menu an item belongs such that multiple menus may be included within a single data storage structure. Next, an item name field provides the name of an item. A price field provides the price of the item. A type of currency field designates the currency that the price is list in. A description field may provide a textual description of the menu item. Fields such as the heart smart field designate overall ratings of the food menu item. An overall dietary daily values field includes a breakdown of the serving size, calories, fat contents, carbohydrates, protein, sodium, vitamins and other dietary values.

An ingredients field provides a list of all ingredients utilized in the preparation of a menu item. In addition, the amounts of each ingredient are designated. Further, additional ingredients making up each ingredient may be included. For example, the ingredients that are utilized to produce brandy may be listed. Additionally, fields are included for designating whether or not an ingredient contains alcohol or caffeine, utilizes organically grown and/or free range products, is prepared kosher or is a vegan-friendly ingredient. In addition, the dietary daily value breakdown for each ingredient is provided. For example, the number of calories provided by ½ lb. of chicken is distinguished. Additional ratings fields for each ingredient may be provided.

Referring now to FIG. 5, there is depicted a block diagram of a storage structure for a selection of food preferences in accordance with the present invention. As illustrated, the data corresponding to a selection of food preferences is preferably stored in a data storage structure such as database 80. The example database 80 is provided in order to depict a selection of fields 72 which may be included in a data storage structure. For the purposes of example, food preferences have been entered for rows 74 and 76. In alternate embodiments, alternate selections of fields for food preferences may be utilized. In addition, alternate types of data storage structures and methods may be utilized. Further, while not depicted, a graphical interface for entering a selection of fields 72 and food preferences is preferably provided by a data processing system such as computer system 10.

As illustrated in FIG. 5, fields 72 include multiple fields that are utilized for filtering a food menu. For example, a user field designates the user of the specifications for a row such that preferences for multiple users may be included. Next, an age field designates the age of each user. The age of the user is preferably automatically incremented from the user's birthdate. The price range field includes price range limits. Price range limits may be set by the user, or may be set automatically by a money management application that tracks the customer's available resources and budgetary constraints. Alternatively, a user may designate a particular price range of breakfasts, lunches and dinners. In addition, the user may designate a particular price range depending on who the user is dining with. A currency preference field designates in which currency the user would prefer to see prices listed.

Further a special instructions field may include other special instructions that the user designates.

Food and health preferences of the user are also included in field 72. Ingredients to avoid field includes ingredients which the user does not want included. Preparation preferences field designates any preparation preferences that the user desires. Health rating preferences field includes multiple fields including alcohol preference, caffeine preference, heart smart meal preference, organic product preference, kosher preparation preference, protein preference, fat preference, calorie preference. Protein preference, fat preferences and calorie preference may be fields that are set by the user or alternatively may be set by a food monitoring program that controls the amount of protein, fat and calories that a user consumes daily.

In addition, a user may designate the level of security that is desired with the data for each user ID. For example, a security preference may block a user ID from being accessed. In another example, a security preference may designate who can access the food preferences and how long the data can be held in an alternate data storage device. As is well known in the art, other types of data security may be designated by the user to protect their food preference data.

Figure 6A:
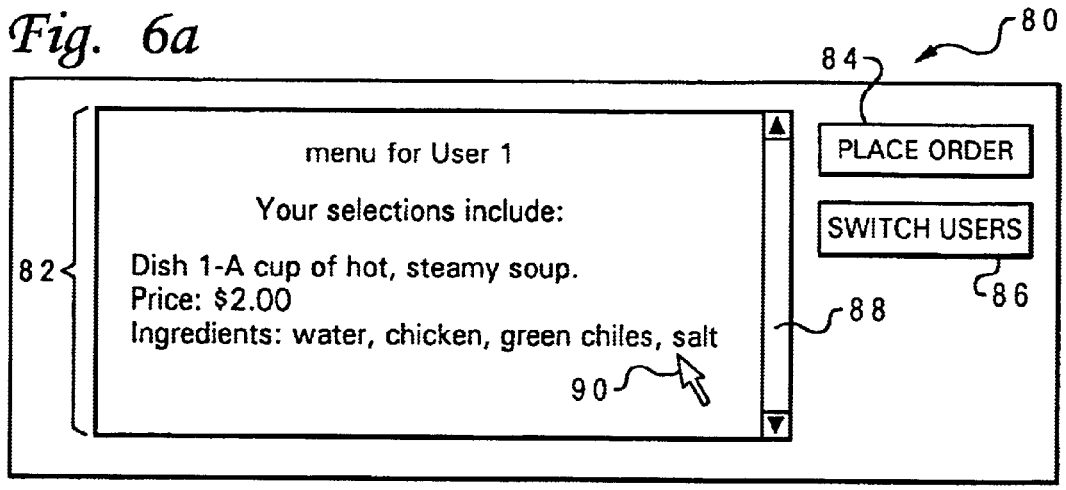
FIGS. 6a–6c illustrate a graphical representation of a specialized electronic food menu in accordance with the method and system of the present invention.
Figure 6B:
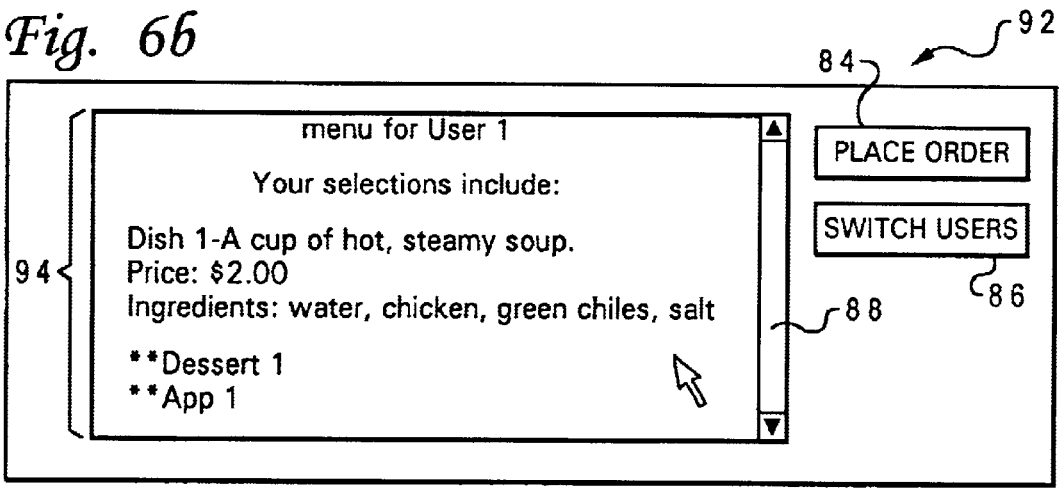
Figure 6C:
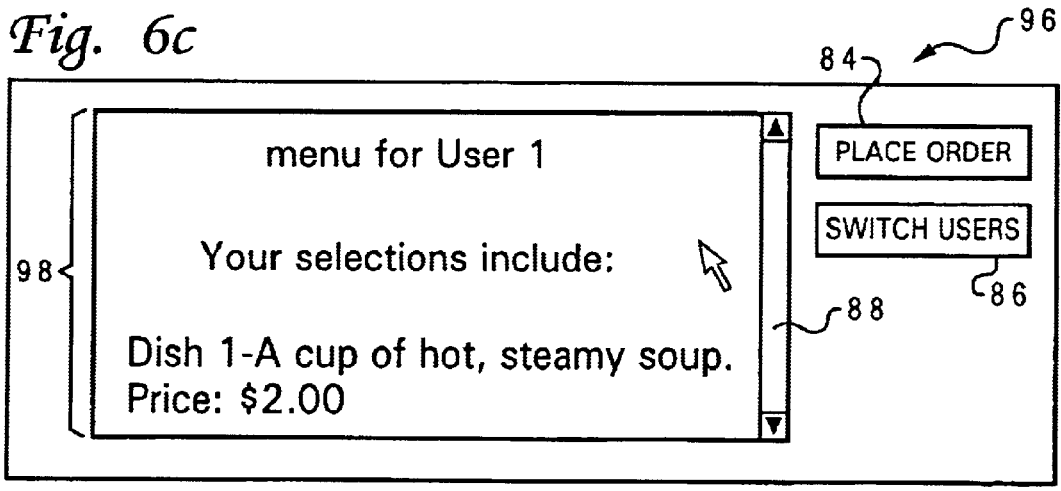

With reference now to FIGS. 6a–6c, there is depicted a graphical representation of a specialized electronic food menu according the method and system of a preferred embodiment of the present invention. In the examples, the specialized electronic food menu is determined by food preferences for user 1. Food preferences for user 1 are depicted at row 74 of FIG. 5 and have preferably been previously stored in a manner that is accessible to computer system 10. In comparing the food menu items illustrated at rows 64 and 66 of FIG. 4 with the user preferences for user 1, "Dish 1" is selected from the menu items.

Referring to FIG. 6a, a graphical display 80 includes a graphical representation 82 of a specialized electronic food menu, wherein graphical representation 82 depicts only the menu items that are selected. In the present example, only Dish 1 meets the customer's food preferences. With reference to FIG. 6b, a graphical display 92 includes a graphical representation 94 of a specialized electronic food menu, wherein graphical representation 94 illustrates all the menu items, however the menu items that are not selected are flagged. In the example, Dessert 1 and App 1 are flagged as not meeting the customer's food preferences. In addition, a description and price of the flagged items is not included. However, in alternate embodiments, the description and price of flagged items may be included. Referring to FIG. 6c, a graphical display 96 includes a graphical representation 98 of a specialized electronic food menu. In the example, an output preferences for user 1 specifies output in a large font size. Therefore, graphical representation 98 illustrates the specialized menu at a particular large font size. Preferably, the user can specify a font size or a range of font sizes for the text of a specialized food menu.

In both embodiments depicted, a user may select the scroll bar 88 in order to scroll through the menu for user 1 utilizing pointing indicator 90. In addition, the user may select from buttons 84 and 86 to perform functions such as placing an order or switching user preferences. In alternate embodiments, alternate types of graphical displays may be provided. In addition, the display is preferably adjusted according to any user display preferences, as previously described. Further, as previously described, while a graphical representation of a specialized electronic food menu is displayed utilizing one rendering method, other rendering methods may be utilized.

Figure 7B:
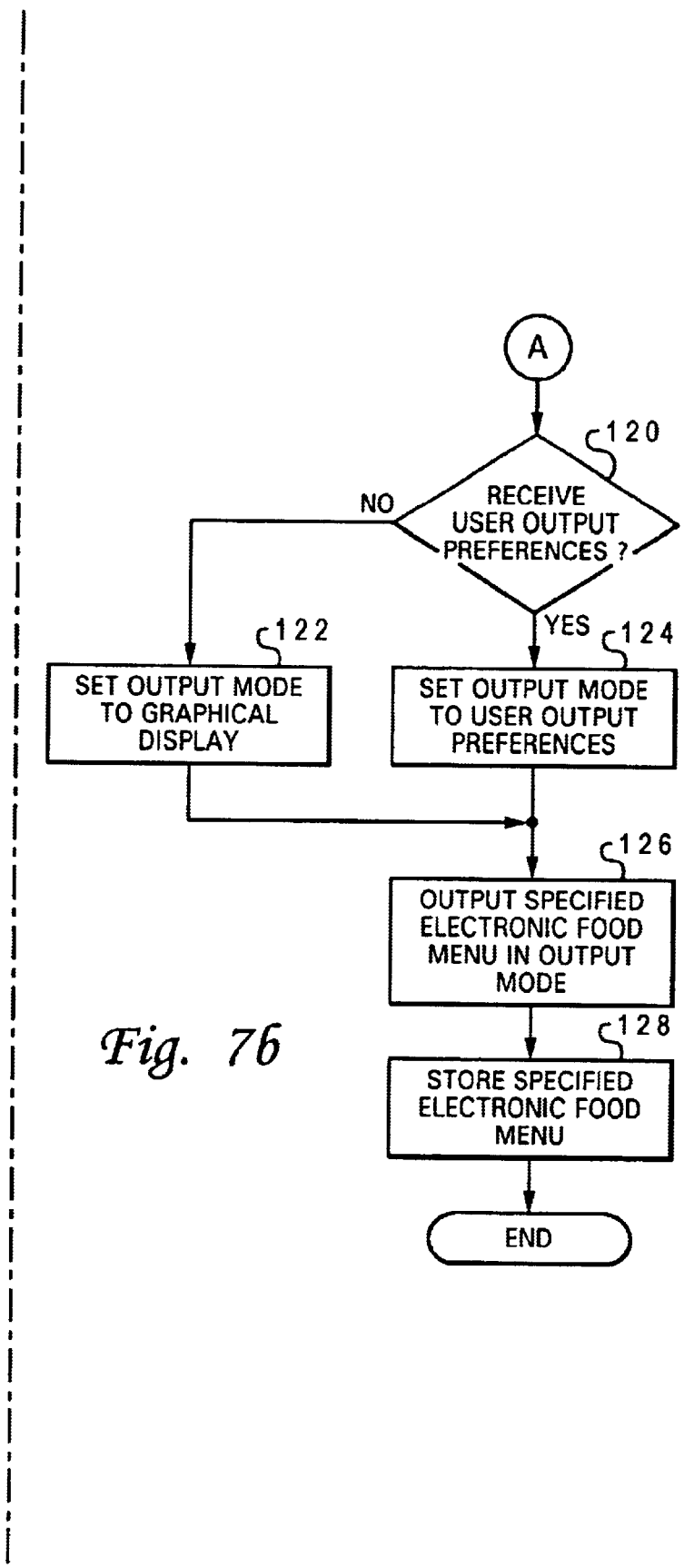
FIG. 7 depicts a high level logic flowchart of a process for specializing an electronic food menu for a particular customer in accordance with the method and system of the present invention.

Referring now to FIG. 7, there is illustrated a high level logic flowchart of a process for specializing an electronic food menu for a particular customer. As depicted, the process starts at block 100 and thereafter proceeds to block 102. Block 102 illustrates a determination as to whether a request to retrieve a food menu is received. If a request to retrieve a food menu is not received, the process iterates at block 102. If a request to retrieve a food menu is received, the process passes to block 104. Block 104 depicts transmitting a request for a food menu. In particular, the request for a food menu is transmitted to a data storage medium via the particular communications media utilized by the computer system performing the process. Next, block 106 illustrates a determination as to whether a connection to the food menu is received. If the connection to the food menu is not yet received, the process passes to block 104. If the connection to the food menu is received, the process passes to block 108.

Block 108 depicts setting the current item to the first food menu item of the food menu received. Next, block 110 illustrates comparing the current item with the food preferences for a particular customer. Thereafter, block 112 depicts a determination as to whether the current item satisfies the food preferences for the particular customer. If the current item does not satisfy the user preferences for the particular customer, the passes to block 113. Block 113 illustrates designating the ingredients that do not satisfy the food preferences. Next, block 115 depicts determining substitute ingredients for those ingredients that do not satisfy the food preferences. The restaurant may provide a list of substitute ingredients with the food menu items or the computer system may include a list of substitute ingredients. If the current item does satisfy the user preferences for the particular customer, the process passes to block 114. Block 114 illustrates designating the current item as a food menu item selection. Thereafter, the process passes to block 116.

Block 116 illustrates a determination as to whether any food menu items remain. If there are not any remaining food menu items, the process passes to block 120. If there are remaining food menu items, the process passes to block 118. Block 118 depicts setting the current item to the next food menu item. Thereafter, the process passes to block 110.

Block 120 depicts a determination as to whether any user output preferences are set for the particular customer. If no user output preferences are set for the particular customer, the process passes to block 122. Block 122 illustrates setting the output mode to a generic graphical display and thereafter the process passes to block 126. If user output preferences are set for the particular customer, the process passes to block 124. Block 124 depicts setting the output mode according to the user output preferences. Thereafter, block 126 illustrates outputting the specified electronic food menu in the output mode, wherein food menu items that satisfy food preferences for the particular customer are distinguishable. Next, block 128 depicts storing the specified electronic food menu. Thereafter, the process ends. As previously described, output preferences may include the color, sequence, size and other graphical distinctions. In addition, output preferences may designate displaying only those food menu items that satisfy user preferences. Moreover, output preferences may indicate what informational data a user wants with the food menu items.

Figure 8:
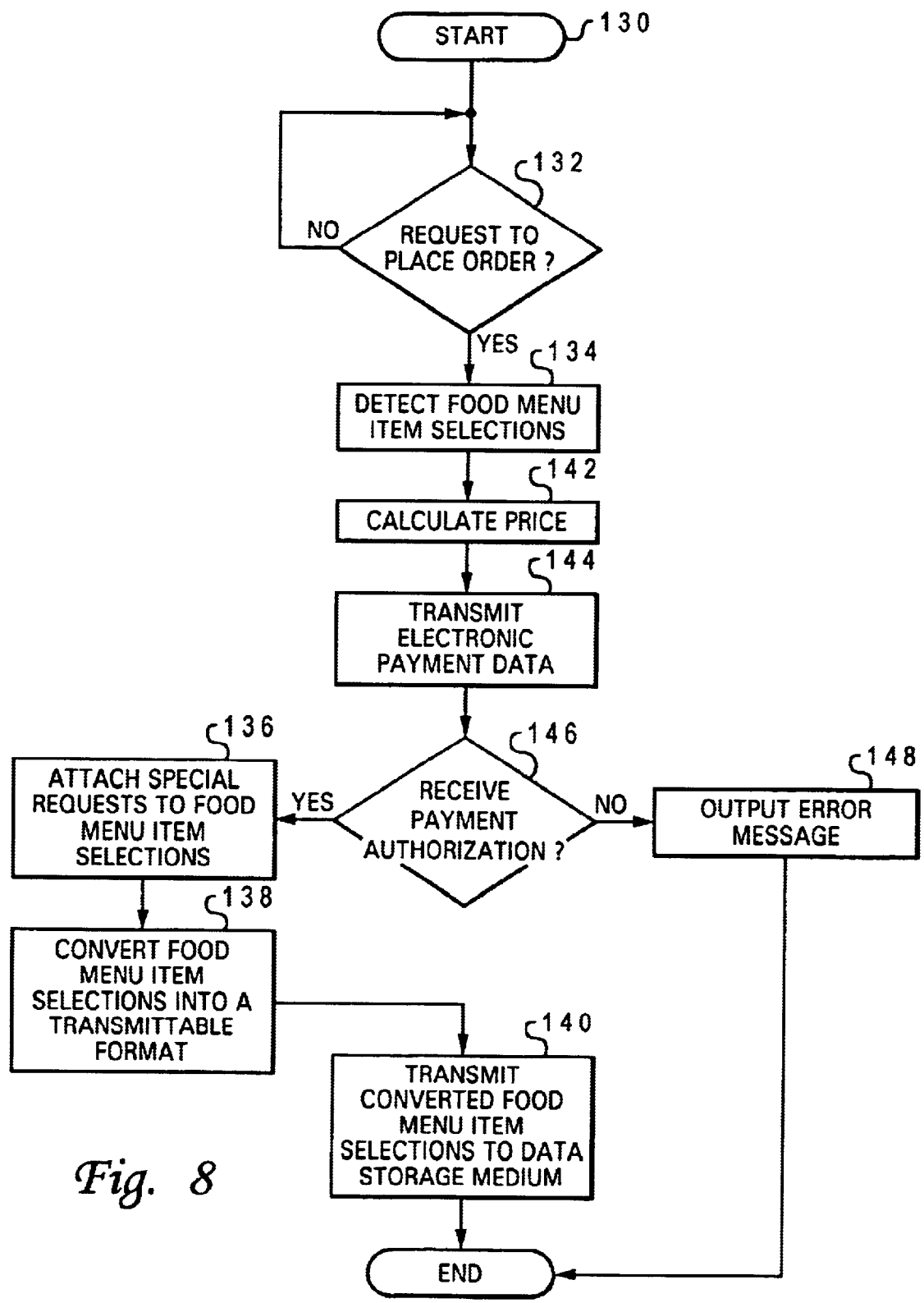
FIG. 8 illustrates a high level logic flowchart of a process for placing a food order in accordance with the method and system of the present invention.

With reference now to FIG. 8, there is depicted a high level logic flowchart of a process for placing a food order. As illustrated, the process starts at block 130 and thereafter proceeds to block 132. Block 132 depicts a determination as to whether a request to place an order is made. Requests to place orders may come from a user selecting an order from a specified electronic food menu or may come from a queued order stored on the customer's computer system. If a request to place an order is not made, the process iterates at block 132. If a request to place an order is made, the process passes to block 134. Block 134 illustrates detecting food menu items that are selected by the user. Next, block 142 depicts calculating a price for the order with adjustment for any electronic coupons being redeemed. Thereafter, block 144 illustrates transmitting electronic payment data. Next, block 146 depicts a determination as to whether payment authorization is received. If payment authorization is not received, the process passes to block 148. Block 148 illustrates outputting an error message and then the process ends. If payment authorization is received, the process passes to block 136.

Block 136 depicts attaching special requests to the food menu items selected by the user. Thereafter, block 138 illustrates converting the food menu items selected by the user into a transmittable format. Next, block 140 depicts transmitting the converted food menu items selected by the user to an order queue of a data storage medium. Thereafter, the process ends. While one embodiment of a process for placing a food order is depicted, alternate processes may be utilized for placing food orders wherein users select from the specialized electronic food menu and that selection is transmitted to an order queue or other order system.

Figure 9:
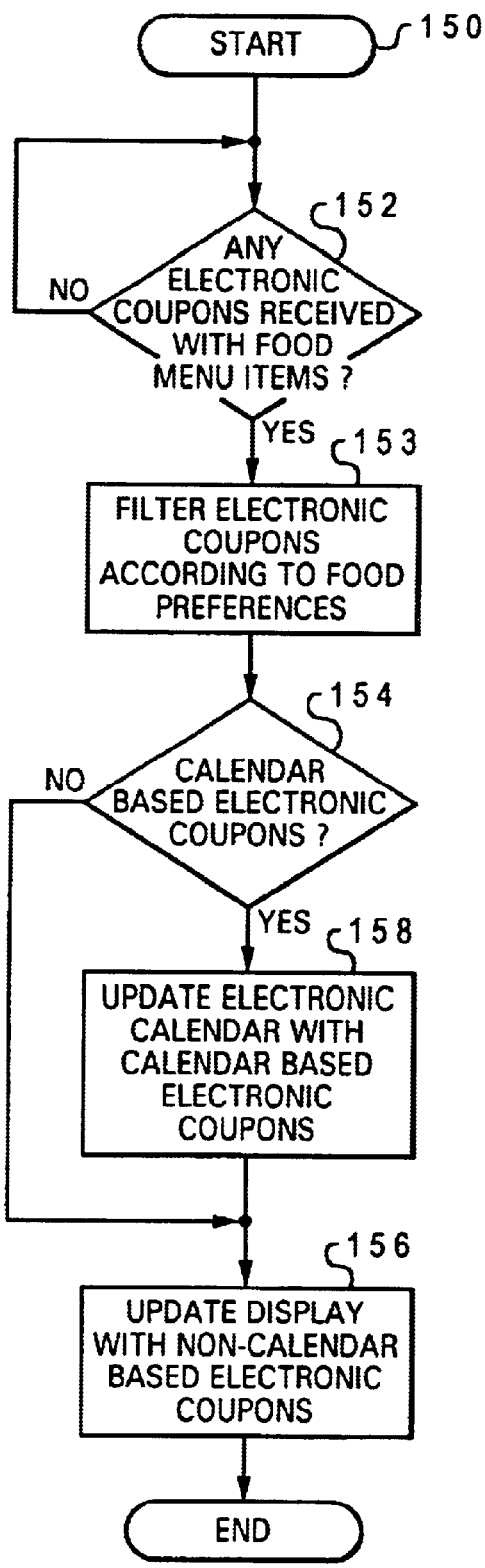
FIG. 9 depicts a high level logic flowchart of a process for presenting electronic coupons.

Referring now to FIG. 9, there is illustrated a high level logic flowchart of a process for presenting electronic coupons. As depicted, the process starts at block 150 and thereafter proceeds to block 152. Block 152 illustrates a determination as to whether any electronic coupons are received with the food menu items. Thereafter, block 153 depicts filtering the electronic coupons according to food preferences. Next, block 154 illustrates a determination as to whether any calendar based electronic coupons are received. If calendar based electronic coupons are received, the process passes to block 158. Block 158 depicts updating an electronic calendar with the calendar based electronic coupons and the process passes to block 156. Block 156 illustrates updating the graphical display with any non-calendar based electronic coupons and the process ends.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for specifying an electronic food menu, said method comprising the steps of:

retrieving a plurality of food menu items from a data storage medium;

comparing said plurality of food menu items with previously stored food preferences for a particular customer;

presenting a food menu, wherein said plurality of food menu items that satisfy said food preferences for said particular customer are designated on said food menu, such that an electronic food menu is specified for a particular customer;

graphically displaying said selected food menu, wherein said plurality of food menu items that do not satisfy said previously stored food preferences for said particular customer are graphically distinguishable from said plurality of food menu items that do satisfy said food preferences for said particular customer.

2. The method for specifying an electronic food menu according to claim 1, said method further comprising the step of:

graphically displaying said selected food menu according to a output preference for said particular customer, such that the graphical representation of said selected food menu is provided to accommodate a display preference for said particular customer.

3. The method for specifying an electronic food menu according to claim 2, said step of graphically displaying said selected food menu further comprising the step of:

graphically displaying only said plurality of food menu items of said selected food menu that are designated.

4. The method for specifying an electronic food menu according to claim 2, said step of graphically displaying said selected food menu further comprising the step of:

graphically displaying said selected food menu in order from designated food menu items to non-designated food menu items.

5. The method for specifying an electronic food menu according to claim 2, said step of graphically displaying said selected food menu further comprising the step of:

graphically displaying a tactile-detectable graphical representation of said selected food menu, wherein said output preference for said particular customer designates a tactile-detectable graphical representation.

6. The method for specifying an electronic food menu according to claim 2, said step of graphically displaying said selected food menu further comprising the step of:

graphically displaying a graphical representation of said selected food menu utilizing a particular font size, wherein said output preference for said particular customer designates said particular font size.

7. The method for specifying an electronic food menu according to claim 2, said step of graphically displaying said selected food menu further comprising the step of:

graphically displaying a graphical representation of said selected food menu utilizing a particular language, wherein said output preference for said particular customer designates said particular language.

8. The method for specifying an electronic food menu according to claim 2, said step of graphically displaying said selected food menu further comprising the step of:

graphically displaying a graphical representation of said selected food menu wherein prices are displayed in a particular currency, wherein said output preference for said particular customer designates said particular currency.

9. The method for specifying an electronic food menu according to claim 1, said method further comprising the step of:

transmitting auditory output of said selected food menu for said particular customer.

10. The method for specifying an electronic food menu according to claim 1, said method further comprising the step of:

graphically printing said selected food menu for said particular customer.

11. The method for specifying an electronic food menu according to claim 1, said method further comprising the step of:

graphically displaying said selected food menu according to a generic style sheet.

12. The method for specifying an electronic food menu according to claim 1, said step of retrieving a plurality of food menu items from a data storage medium, further comprising the step of:

receiving said plurality of food menu items via a wireless transmission medium.

13. The method for specifying an electronic food menu according to claim 12, said step of retrieving a plurality of food menu items from a data storage medium, further comprising the step of:

receiving said plurality of food menu items via a radio frequency transmission medium.

14. The method for specifying an electronic food menu according to claim 13, said step of receiving said plurality of food menu items in a data transmission protocol, further comprising the step of:

transmitting said food menu items in an extensible markup language protocol.

15. The method for specifying an electronic food menu according to claim 12, said step of retrieving a plurality of food menu items from a data storage medium, further comprising the step of:

receiving said plurality of food menu items via an infrared connection.

16. The method for specifying an electronic food menu according to claim 1, said step of retrieving a plurality of food menu items from a data storage medium, further comprising the step of:

receiving said plurality of food menu items in a data transmission protocol.

17. The method for specifying an electronic food menu according to claim 1, said step of retrieving a plurality of food menu items from a data storage medium, further comprising the step of:

accessing a plurality of food menu items from a database, wherein each of said plurality of food menu items comprises a plurality of food and health identifiers.

18. The method for specifying an electronic food menu according to claim 17, said step of transmitting said previously stored food preferences further comprising the step of:

determining electronic coupons to provide to a particular customer from said previously stored food preferences.

19. The method for specifying an electronic food menu according to claim 1, said method further comprising the step of:

transmitting said previously stored food preferences for said particular customer to said data storage medium for storage.

20. The method for specifying an electronic food menu according to claim 19, said method further comprising the step of:

confirming electronic payment for said order.

21. The method for specifying an electronic food menu according to claim 19, said method further comprising the step of:

adjusting a waiting period for said order in accordance with said food preferences for said particular customer.

22. The method for specifying an electronic food menu according to claim 21, said method further comprising the step of:

filtering said electronic coupons that are displayed to a particular customer according to said food preferences for said particular customer.

23. The method for specifying an electronic food menu according to claim 22, said method further comprising the step of:

retrieving electronic coupons that are specified for said plurality of customers.

24. The system for specifying an electronic food menu according to claim 23, wherein said graphical display monitor only displays said plurality of food menu items of said selected food menu that are designated.

25. The system for specifying an electronic food menu according to claim 23, wherein said graphical display monitor displays said selected food menu items in order from designated food menu items to non-designated food menu items.

26. The system for specifying an electronic food menu according to claim 23, wherein said graphical display monitor displays said specified food menu such that said plurality of food menu items that do not satisfy said previously stored food preferences for said particular customer are graphically distinguishable from said plurality of food menu items that do satisfy said food preferences for said particular customer.

27. The system for specifying an electronic food menu according to claim 23, wherein said graphical display monitor displays a tactile-detectable graphical representation of said selected food menu.

28. The system for specifying an electronic food menu according to claim 23, wherein said graphical display monitor displays a graphical representation of said selected food menu utilizing a particular font size.

29. The system for specifying an electronic food menu according to claim 23, wherein said graphical display monitor displays a graphical representation of said selected food menu utilizing a particular language.

30. The system for specifying an electronic food menu according to claim 23, wherein said graphical display monitor displays a graphical representation of said selected food menu wherein said prices are depicted utilizing a particular currency.

31. The method for specifying an electronic food menu according to claim 21, said method further comprising the step of:

updating an electronic calendar with said electronic coupons that are specified for a particular time period.

32. The method for specifying an electronic food menu according to claim 1, said method further comprising the steps of:
receiving an order from said particular customer for food menu items from said selected food menu; and
transmitting said order to an order retrieval system.

33. The method for specifying an electronic food menu according to claim 1, said method further comprising the step of:
updating an electronic calendar with said designated food menu items that are specified in said food preferences for a particular time period.

34. The method for specifying an electronic food menu according to claim 1, said step of retrieving said plurality of food menu items from said data storage medium further comprises the step of:
retrieving electronic coupons for said plurality of food menu items from said data storage medium.

35. The method for specifying an electronic food menu according to claim 1, said method further comprising the steps of:
comparing said plurality of food menu items with a plurality of previously stored food preferences for a plurality of customers; and
selecting a food menu wherein said plurality of food menu items that satisfy said previously stored food preferences for said plurality of customers are distinguished, such that an electronic food menu is specified for said plurality of customers.

36. The system for specifying an electronic food menu according to claim 35, said system further comprising:
a graphical display monitor for displaying said selected food menu according to an output preference for said particular customer, such that the graphical representation of said food menu is provided to accommodate a display preference of said particular customer.

37. The system for specifying an electronic food menu according to claim 35, system further comprising:
an audio element for transmitting auditory output of said selected food menu for said particular customer.

38. The system for specifying an electronic food menu according to claim 35, said system further comprising:
a printing element for graphically printing said selected food menu for said particular customer.

39. The system for specifying an electronic food menu according to claim 38, wherein said wireless communication element supports communication via a radio frequency transmission.

40. The system for specifying an electronic food menu according to claim 38, wherein said wireless communication element supports communication via an infrared transmission.

41. The system for specifying an electronic food menu according to claim 35, said system further comprising:
a graphical display monitor for displaying a graphical representation of said selected food menu according to a generic style sheet.

42. The system for specifying an electronic food menu according to claim 35, wherein said means for retrieving a plurality of food menu items from said data storage medium, further comprises:
a wireless communication element for receiving said plurality of food menu items via a wireless transmission medium.

43. The system for specifying an electronic food menu according to claim 35, wherein said means for retrieving a plurality of food menu items from said data storage medium, further comprises:
a network element for receiving said plurality of food menu items via a network connection.

44. The system for specifying an electronic food menu according to claim 35, wherein said means for retrieving a plurality of food menu items from said data storage medium, further comprises:
a socket interface for receiving said plurality of food menu items via a wired connection.

45. The system for specifying an electronic food menu according to claim 35, wherein said means for retrieving a plurality of food menu items from said data storage medium, further comprises:
a data transmission protocol for specifying data transmissions across said communications medium.

46. The system for specifying an electronic food menu according to claim 35, wherein said data transmission protocol is an extensible mark-up language protocol.

47. The system for specifying an electronic food menu according to claim 35, wherein said data storage medium further comprises:
a plurality of food menu items accessible from a database, wherein each of said plurality of food and health identifiers.

48. The system for specifying an electronic food menu according to claim 35, said system further comprising:
a local data storage medium comprising said previously stored food preferences for said particular customer, wherein said previously stored food preferences for a particular customer comprise a plurality of food and health ratings.

49. The system for specifying an electronic food menu according to claim 35, said system further comprising:
means for transmitting said previously stored food preferences for said particular customer to said data storage medium.

50. The system for specifying an electronic food menu according to claim 35, said data processing system further comprising:
a local data storage medium for storing said selected food menu, such that said selected food menu is recallable from said local data storage medium.

51. The system for specifying an electronic food menu according to claim 50, wherein said data processing system requests confirmation of an electronic payment for said order.

52. The system for specifying an electronic food menu according to claim 35, wherein said data processing system comprises a pervasive data processing system.

53. The system for specifying an electronic food menu according to claim 35, wherein said data processing system transmits an order to an order queue of food menu items from said selected menu that are selected by said particular customer.

54. The system for specifying an electronic food menu according to claim 35, wherein said data processing system further comprises an electronic calendar that is updated with food menu items that are designated for a particular time period.

55. The system for specifying an electronic food menu according to claim 35, wherein said data storage medium further comprises a plurality of electronic coupons for said plurality of food menu items.

56. The program according to claim 55, said program further comprising:

means for enabling a graphical display of said plurality of food menu items, wherein said plurality of food menu items that do not satisfy said previously stored preferences are graphically designated.

57. The program according to claim 55, said program further comprising:
means for enabling said graphical display of said generated food menu according to an output preference for said particular customer.

58. The program according to claim 55, said program further comprising:
means for enabling auditory output of said generated food menu for said particular customer.

59. The program according to claim 55, said program further comprising:
means for enabling tactile-detectable output of said generated food menu for said particular customer.

60. The program according to claim 55, said program further comprising:
means for transmitting said previously stored food preferences for said particular customer to said data storage medium.

61. The program according to claim 55, said program further comprising:
means for receiving an order from said particular customer of selected food menu items from among said selected food menu; and
means for transmitting said order to an order retrieval system.

62. The program according to claim 55, said program further comprising:
means for designating those food menu items that do not meet said food preferences.

63. The program according to claim 55, wherein said food preferences includes health rating preferences for said particular customer.

64. The program according to claim 55, wherein said food preferences includes attributes of specified allowable ingredients and specified avoided ingredients for said particular customer.

65. The system for specifying an electronic food menu according to claim 35, wherein said data processing system further comprises:
means for comparing said plurality of food menu items with a plurality of previously stored food preferences for a plurality of customers; and
means for selecting a food menu wherein said plurality of food menu items that satisfy said previously stored food preferences for said plurality of customers are distinguished, such that an electronic food menu is specified for said plurality of customers.

66. The system for specifying an electronic food menu according to claim 35, said system further comprising:
means for designating those food menu items that do not meet said food preferences.

67. The system for specifying an electronic food menu according to claim 35, wherein said food preferences includes health rating preferences for said particular customer.

68. The system for specifying an electronic food menu according to claim 35, wherein said food preferences includes attributes of specified allowable ingredients and specified avoided ingredients for said particular customer.

69. The method for specifying an electronic food menu according to claim 1, said method further comprising the step of:
designating those food menu items that do not meet said food preferences.

70. The method for specifying an electronic food menu according to claim 1, wherein said food preferences includes health rating preferences for said particular customer.

71. The method for specifying an electronic food menu according to claim 1, wherein said food preferences includes attributes of specified allowable ingredients and specified avoided ingredients for said particular customer.

72. A system for specifying an electronic food menu, said system comprising:
a data storage medium comprising a plurality of food menu items;
a data processing system with access to said data storage medium;
a graphical display monitor for displaying said specified food menu such that said plurality of food menu items that do not satisfy said previously stored food preferences for said particular customer are graphically distinguishable from said plurality of food menu items that do satisfy said food preferences for said particular customer;
wherein said data processing system comprises:
a communications medium for retrieving said plurality of food menu items from said data storage medium;
means for comparing said plurality of food menu items with a plurality of previously stored food preferences for a particular customer;
means for presenting a food menu wherein said plurality of food menu items that satisfy said previously stored food preferences for said particular customer are distinguished on said food menu, such that an electronic food menu is specified for a particular customer.

73. A program, residing on a computer usable medium having computer readable program code means, said program comprising:
means for retrieving a plurality of food menu items from a data storage medium;
means for comparing said plurality of food menu items with previously stored food preferences for a particular customer; and
means for generating a food menu designating a selection of said plurality of food menu items that satisfy said previously stored food preferences for said particular customer; and
means for graphically displaying said selected food menu, wherein said plurality of food menu items that do not satisfy said previously stored food preferences for said particular customer are graphically distinguishable from said plurality of food menu items that do satisfy said food preferences for said particular customer.

74. A method for specifying an electronic food menu, said method comprising the steps of:
retrieving a plurality of food menu items from a data storage medium;
comparing said plurality of food menu items with previously stored food preferences for a particular customer; and
presenting a food menu, wherein said plurality of food menu items that are indicated to be avoided by said food preferences for said particular customer are designated, such that a customized electronic food menu is specified for a particular customer.

75. A system for specifying an electronic food menu, said system comprising:

a data storage medium comprising a plurality of food menu items;

a data processing system with access to said data storage medium;

wherein said data processing system comprises:

a communications medium for retrieving said plurality of food menu items from said data storage medium;

means for comparing said plurality of food menu items with a plurality of previously stored food preferences for a particular customer; and means for presenting a food menu, wherein said plurality of food menu items that are indicated to be avoided by said previously stored food preferences for said particular customer are distinguished, such that a customized electronic food menu is specified for a particular customer.

76. A program, residing on a computer usable medium having computer readable program code means, said program comprising:

means for retrieving a plurality of food menu items from a data storage medium;

means for comparing said plurality of food menu items with previously stored food preferences for a particular customer; and means for generating a food menu designating a selection of said plurality of food menu items indicated to be avoided by said previously stored food preferences for said particular customer.

* * * * *